United States Patent [19]

Nielsen

[11] Patent Number: 4,571,255
[45] Date of Patent: Feb. 18, 1986

[54] SUBSITUTED PHENOXYBENZISOXAZOLE HERBICIDES

[75] Inventor: Donald R. Nielsen, Wadsworth, Ohio

[73] Assignee: PPG Industries, Inc., Pittsburgh, Pa.

[21] Appl. No.: 566,745

[22] Filed: Dec. 29, 1983

[51] Int. Cl.$^4$ .................... C07D 261/20; A01N 31/08
[52] U.S. Cl. ........................................... 71/88; 548/241
[58] Field of Search ............................ 548/241; 77/88

[56] References Cited

U.S. PATENT DOCUMENTS

| | | | |
|---|---|---|---|
| 4,344,789 | 8/1982 | Krass et al. | 71/121 |
| 4,375,981 | 3/1983 | Krass et al. | 71/121 |
| 4,472,425 | 9/1984 | Sandmeier et al. | 548/240 |

FOREIGN PATENT DOCUMENTS

| | | | |
|---|---|---|---|
| 5246286 | 11/1977 | Japan | 71/121 |
| 898916 | 6/1962 | United Kingdom | 71/121 |

Primary Examiner—Donald G. Daus
Assistant Examiner—G. Hendricks
Attorney, Agent, or Firm—Edward J. Whitfield

[57] ABSTRACT

This invention relates to herbicidally active substituted phenoxybenzisoxazole derivatives and to the use of such compound to control the growth of noxious plants, i.e., weeds.

4 Claims, No Drawings

SUBSTITUTED PHENOXYBENZISOXAZOLE HERBICIDES

FIELD OF THE INVENTION

This invention relates to herbicidally active substituted phenoxybenzisoxazole compounds and to the use of such compounds to control the growth of noxious plants, i.e., weeds.

DESCRIPTION OF THE INVENTION

This invention provides herbicidally active substituted phenoxybenzisoxazole compounds represented by the Formula I:

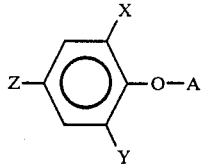

wherein: A is a benzisoxazole radical selected from:

(a) 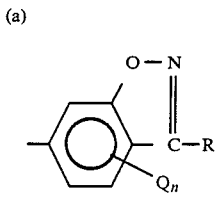 (b) 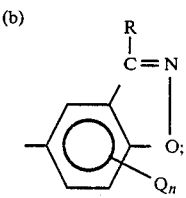

(c) 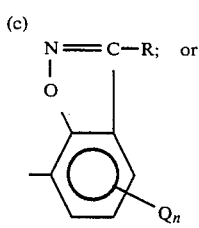 (d) 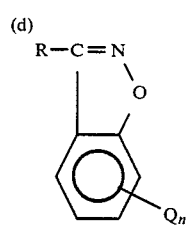

wherein:

X and Y are hydrogen, halogen, $C_1$ to $C_4$ haloalkyl, nitro or cyano;

Z is halogen, $C_1$ to $C_4$ alkylsulfonyl, aminosulfonyl or $C_1$ or $C_4$ haloalkyl;

R is hydrogen, halogen, cyano, amino, mono- or dialkylamino, hydroxy, $C_1$ to $C_4$ alkyl or haloalkyl, $C_1$ to $C_4$ alkoxy, haloalkoxy or alkylthio, phenyl or substituted phenyl, phenoxy or substituted phenoxy, carboxy or alkoxycarbonyl;

Q is halogen, nitro, cyano or $C_1$ to $C_4$ haloalkyl; and n is 0, 1, 2, or 3.

Suitable alkyl radicals of which the various substituents are representative include methyl, ethyl, n-propyl, iso-propyl, n-butyl, t-butyl or iso-butyl. Chloromethyl, chloroethyl, bromomethyl, bromoethyl, trifluoromethyl and the like are exemplary haloalkyls. As examples of alkoxy and alkylthio radicals there may be mentioned methoxy, ethoxy, propoxy, thiomethyl, thioethyl or the like. Mono or dialkyl amino groups include methylamino, dimethylamino, methylethylamino, diethylamino or the like. Halogens represented by X, Y, Z and R include bromine, chlorine or fluorine. 2-propenyl and 2-propynyl are exemplary of preferred alkenyl and alkynyl radicals.

Preferred compounds of the Formula I are those wherein X or Y is halogen, e.g., chlorine; Z is trifluoromethyl and R is alkyl.

Compounds of the Formula I may be prepared using techniques known to and starting materials available to the art. For example, a Formula I compound may be prepared by reacting, with an alkali metal carbonate, an appropriately substituted diphenyl ether oxime of the Formula II.

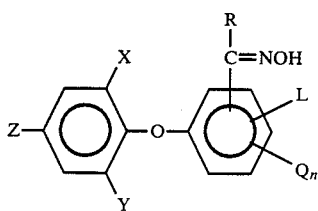

wherein X, Y, Z, R and $Q_n$ are as previously defined and L is a "leaving" group, e.g., halogen, alkyl, acyloxy, aryl sulfonate, nitro or the like, wherein L and C(R)=NOH are ortho each to the other, i.e., they occupy adjacent ring positions.

More particularly, the Formula II compound is reacted with potassium carbonate in a suitable organic solvent, e.g., acetonitrile, dimethylformamide, dimethylsulfoxide or the like at temperature up to reflux for a time sufficient to obtain the desired extent of conversion.

Alternatively, rather than using as a starting material a fully formed diphenyl ether oxime of the Formula II, a suitably substituted benzoxime compound, e.g., 5-hydroxy-2-nitro acetophenone oxime, is first converted to the corresponding benzisoxazole by reaction with potassium carbonate and then coupled in known fashion with a compatible benzo compound, e.g., 3-chloro-4-fluorobenzotrifluoride, to form a phenoxybenzisoxazole compound of the Formula I.

The preparation of certain Formula I compounds are illustrated by the following examples:

EXAMPLE I

Preparation of 5-(2-chloro-4-trifluoromethylphenoxy)-3-methylbenzisoxazole

To a flask provided with a magnetic bar and a reflux condenser was charged 7.49 grams (0.02 mole) of 5-(2-chloro-4-trifluoromethylphenoxy)-2-nitroacetophenone oxime, 3.32 grams (0.024 mole) of ground potassium carbonate and 50 milliliters of acetonitrile. The stirred reaction mixture was refluxed for about 29 hours and solvent was then evaporated at reduced pressure. The residue was slurried with 100 milliliters of methylene chloride and suction filtered. The filtrate was evaporated to a volume of 60 milliliters and diluted with 60 milliliters of benzene. The mixture was then filtered, washed with water and evaporated at reduced pressure affording 2.83 grams of residue identified by MS and NMR analyses as the desired product.

EXAMPLE II

Preparation of 6-(2-chloro-4-trifluoromethylphenoxy)-3-methylbenzisoxazole

A stirred mixture of 2.00 grams (0.0134 mole) of 3-methyl-6-hydroxybenzisoxazole, 2.96 grams (0.0149 mole) of 3-chloro-4-fluorobenzotrifluoride, 2.60 grams (0.0188 mole) of potassium carbonate and 50 milliliters of dimethylsulfoxide was heated at 70° C. for about 5.5 hours. The reaction mixture was then filtered and most of the solvent was removed from the filtrate by distillation at reduced pressure. The residue was added to water and extracted with methylene chloride. Evaporation of solvent afforded 2.91 grams of residue identified by MS and NMR analyses as the desired product.

Although the invention has been illustrated by the foregoing Example with regard to the preparation of a specific compound within the scope of Formula I, it is to be understood that other compounds within the scope of Formula I may readily be prepared by those skilled in the art simply by varying the choice of starting materials and using the same or similar techniques.

Weed control in accordance with this invention is effected by applying to the soil before emergence of weeds therefrom or to the plant after emergence from the soil, a herbicidally effective amount of a compound of this invention. It is, of course, to be understood that the term "a compound of this invention" also includes mixtures of such compounds.

The term "herbicidally effective amount" is that amount of a compound of this invention required to so injure or damage weeds such that the weeds are incapable of recovering following application. The quantity of a compound of this invention applied in order to exhibit a satisfactory herbicidal effect may vary over a wide range and depends on a variety of factors, such as, for example, hardiness of a particular weed species, extend of weed infestation, climatic conditions, soil conditions, method of application, and the like. As little as one or less pound per acre of a compound of this invention could be expected to provide satisfactory weed control, although in some instances application rates in excess of one pound per acre; e.g., up to 5 or more pounds per acre might be required. Of course, the efficacy of a particular compound against a particular weed species may readily be determined by routine laboratory or field testing in a manner well known to the art. It is expected that satisfactory weed control can be had at a rate of application in the range of 1.0 to 2.0 pounds per acre.

Of course, a compound of this invention can be formulated according to routine methods with any of several known and commonly used herbicidal diluents, adjuvants and carriers. The formulations can contain liquid carriers and adjuvants such as organic solvents, as well as emulsifiers, stabilizers, dispersants, suspending agents, spreaders, penetrants, wetting agents and the like. Typical carriers utilized in dry formulations include clay, talc, diatomaceous earth, silica and the like. Preferred formulations are those in the form of wettable powders, flowables, dispersible granulates or aqueous emulsifiable concentrates which can be diluted with water at the site of application. Also, dry formulations such as granules, dusts, and the like, may be used.

When desired, a compound of this invention can be applied in combination with other herbicidal agents in an effort to achieve even broader vegetative control. Typical herbicides which can be conveniently combined with Formula I compound include atrazine, hexazinone, metribuzin, ametryn, cyanazine, cyprazine, prometon, prometryn, propazine, simazine, terbutryn, propham, alachlor, acifluorfen, bentazon, metolachlor and N,N-dialkyl thiocarbamates such as EPTC, butylate or vernolate. These, as well as other herbicides described, for example, in the *Herbicide Handbook of the Weed Science Society of America* may be used in combination with a compound or compounds of the invention. Typically such formulations will contain from about 5 to about 95 percent by weight of a compound of this invention.

The herbicial formulations contemplated herein can be applied by any of several methods known to the art. Generally, the formulation will be surface applied as an aqueous spray. Such application can be carried out by conventional ground equipment, or if desired, the sprays can be aerially applied. Soil incorporation of such surface applied herbicides is accomplished by natural leaching, and is of course facilitated by natural rainfall and melting snow. If desired, however, the herbicides can be incorporated into the soil by conventional tillage means.

Compounds of this invention are believed effective for preemergenece or postemergence control of a wide variety of broadleaf and grassy weeds. Typical of the various species of vegatative growth that may be controlled, combated, or eliminated are, for example, annuals such as pigweed, lambsquarters, foxtail, crabgrass, wild mustard, field pennycress, ryegrass, goose grass, chickweed, wild oats, velvetleaf, purslane, barnyardgrass, smartweed, knotweed, cocklebur, kochia, medic, ragweed, hemp nettle, spurrey, pondweed, carpetweed, morningglory, ducksalad, cheatgrass, fall panicum, jimsonweed, witchgrass, watergrass, wild turnip, and similar annual grasses and weeds. Biennials that may be controlled include wild barley, campion, burdock, bull thistle, roundleaved mallow, purple star thistle, and the like. Also controlled by the compounds of this invention are perennials such as quackgrass, Johnsongrass, Canada thistle, curley dock, field chickweed, dandelion, Russian knapweed aster, horetail ironweed, seabania, cattail, wintercress, horsenettle, nutsedge, milkweed, sicklepod, and the like.

The compound prepared as described in Example I was tested for herbicial efficacy, against a variety of broadleaf and grassy weed species, under controlled laboratory conditions of light, humidity and temperature. Solvent solutions of the compound were applied, both preemergence and postemergence, to test flats containing the various weed species, and herbicidal efficacy was determined by visual inspection, periodically after application of the compounds. Herbicidal efficacy was determined on a scale of from 0 (no injury) to 10 (11 plants dead). More particularly, the compound of Example I was found effective at a rate of application of 1.0 pound per acre in preemergence control of teaweed, wild mustard, coffeeweed, velvetleaf, yellow foxtail, and Johnsongrass, herbicidal injury ratings in the range of 7 to 8 having been observed up to 22 days subsequent to application.

As a postemergence rate of application of 1.0 pound per acre, the compound of the Example was found effective, particularly against broadleaved weeds, i.e., teaweed, jimsonweed, wild mustard, coffeeweed and velvetleaf, herbicidal injury ratings of from 7 to 10 having been observed up to 22 days subsequent to application.

Although the invention has been described in considerable detail by the foregoing, it is to be understood that many variations may be made therein by those skilled in the art without departing from the spirit and scope thereof as defined by the appended claims.

I claim:

1. A compound represented by the formula:

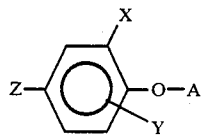

wherein:

A is a benzisoxazole radical selected from:

(a) 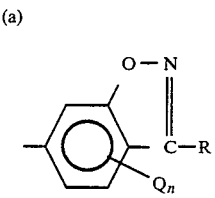  (b) 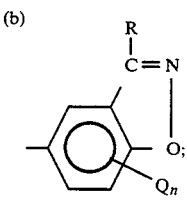

(c) 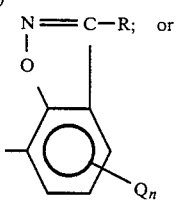  or  (d) 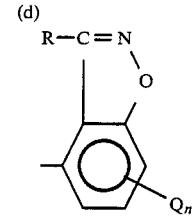

wherein:
X and Y are hydrogen, halogen, $C_1$ to $C_4$ haloalkyl, nitro or cyano;
Z is halogen, $C_1$ to $C_4$ alkylsulfonyl, aminosulfonyl or $C_1$ or $C_4$ haloalkyl;
R is hydrogen, halogen, cyano, amino, mono- or dialkylamino, hydroxy, $C_1$ to $C_4$ alkyl or haloalkyl, $C_1$ to $C_4$ alkoxy, haloalkoxy or alkylthio, phenyl or substituted phenyl, phenoxy or substituted phenoxy, carboxy or alkoxycarbonyl;
Q is halogen, nitro, cyano or $C_1$ to $C_4$ haloalkyl; and $n=0-2$.

2. A compound of claim 1 that is 6-(2-chloro-4-trifluoromethylphenoxy)-3-methyl benzisoxazole or 5-(2-chloro-4-trifluoromethylphenoxy)-3-methyl benzisoxazole.

3. A herbicidal composition containing an agronomically acceptable carrier and a herbicidally effective amount of a compound or mixture of compounds defined in claim 1.

4. In a method of controlling weeds wherein a herbicidally effective amount of herbicide is applied to a growth medium prior to emergence of the weeds therefrom or the weeds subsequent to their emergence from the growth, medium, wherein the improvement resides in using as the herbicide a compound or mixture of compounds defined by claim 1.

* * * * *